(12) United States Patent
Kim et al.

(10) Patent No.: US 9,351,950 B2
(45) Date of Patent: May 31, 2016

(54) METHOD FOR PREVENTING OR TREATING ALLERGIC DISEASE USING CAPSIATE OR SALT THEREOF

(71) Applicant: CATHOLIC UNIVERSITY OF KOREA INDUSTRY-ACADEMIC COOPERATION FOUNDATION, Seoul (KR)

(72) Inventors: Tae-Yoon Kim, Seoul (KR); Yun Sang Lee, Seoul (KR)

(73) Assignee: The Catholic University of Korea Industry-Academic Cooperatior, Seoul (KR)

( * ) Notice: Subject to any disclaimer, the term of this patent is extended or adjusted under 35 U.S.C. 154(b) by 0 days.

(21) Appl. No.: 14/728,682

(22) Filed: Jun. 2, 2015

(65) Prior Publication Data
US 2015/0342919 A1    Dec. 3, 2015

(30) Foreign Application Priority Data
Jun. 3, 2014 (KR) ........................ 10-2014-0067769

(51) Int. Cl.
*A61K 31/231* (2006.01)

(52) U.S. Cl.
CPC ..................................... *A61K 31/231* (2013.01)

(58) Field of Classification Search
CPC ..................................................... A61K 31/231
See application file for complete search history.

(56) References Cited

U.S. PATENT DOCUMENTS

| 6,589,520 B1 * | 7/2003 | Hoppe | ................. | A61K 31/231 424/401 |
| 2011/0028547 A1 * | 2/2011 | Shin | ....................... | A61K 31/04 514/549 |

* cited by examiner

*Primary Examiner* — Brian J Davis
(74) *Attorney, Agent, or Firm* — H.C. Park & Associates, PLC

(57) ABSTRACT

The present invention relates to a method for preventing, alleviating or treating allergic diseases using capsiate or a pharmaceutically acceptable salt thereof. Capsiate or a pharmaceutically acceptable salt thereof according to the present invention may be used for the purpose of preventing, alleviating or treating allergic diseases.

2 Claims, 9 Drawing Sheets

METHOD FOR PREVENTING OR TREATING ALLERGIC DISEASE USING CAPSIATE OR SALT THEREOF

CROSS-REFERENCE TO RELATED APPLICATION

This application claims priority from and the benefit of Korean Patent Application No. 10-2014-0067769, filed on Jun. 3, 2014, which is hereby incorporated herein by reference in its entity.

BACKGROUND

1. Field

The present invention relates to a method for preventing and treating allergic diseases using capsiate or a salt thereof, and more specifically, to a method for preventing, alleviating, or treating allergic diseases, the method comprising administering to or contacting with a subject in need thereof an effective amount of capsiate represented by chemical formula 1 or a salt thereof.

2. Discussion of Background Art

Capsiate as a capsaicin analogue is a kind of capsaicinoid that is mainly found in CH19 Sweet, which is a variety of mildly spicy pepper. Capsiate also activates capsaicin receptors to exhibit equivalent efficacy to capsaicin, such as inhibiting the accumulation of body fat. Capsiate is mildly spicy, and several researches on the mechanism thereof are being carried out, but no concrete achievement has yet been obtained.

Meanwhile, mast cells have been known as intrinsic cells causing several diseases such as allergic rhinitis, allergic atopic dermatitis, allergic conjunctivitis, allergic asthma, food allergies, and anaphylactic shock. These cells are main effector cells that have Fc epsilon receptor 1 (FcεRI) on their surfaces, which is a receptor for an allergy inducing antibody immunoglobulin E (IgE), and mediate a type 1 allergic reaction. The allergic reaction is activated when an antigen contacts an antibody binding to this receptor. There are various methods for treating allergies, but most studies on allergic treatments today are focused on relieving the symptoms instead of removing allergic causes.

Representatively, antagonists of receptors, such as those of histamine and leukotriene, which are secreted from mast cells by allergens, are primary drugs that build a huge market. However, since these drugs show resistance soon after their administration to patients, most drugs do not improve the symptoms of patients after a certain period of time or after repetitive administration. Therefore, the development of anti-allergy medications that does not induce side effects, as found in antihistamines or the like, is being demanded.

Hence, the present inventors, while researching physiological functions of capsiate, have found that capsiate possesses a novel function of inhibiting an allergic reaction caused by the activity of mast cells, and developed a method for preventing or treating allergic diseases using capsiate or a salt thereof, and thus, have completed the present invention.

SUMMARY

An aspect of the present invention is to provide a method for preventing or treating allergic diseases, the method comprising administering to a subject in need thereof an effective amount of capsiate or a pharmaceutically acceptable salt thereof.

Another aspect of the present invention is to provide a method for preventing, alleviating, or treating allergic skin diseases, the method comprising contacting with a subject in need thereof an effective amount of capsiate or a salt thereof.

Therefore, the present invention provides a method for preventing or treating allergic diseases using capsiate or a salt thereof. The capsiate or salt thereof according to the present invention can be used for the purpose of preventing, alleviating, or treating allergic diseases.

DETAILED DESCRIPTION OF THE ILLUSTRATED EMBODIMENTS

Figure 1:
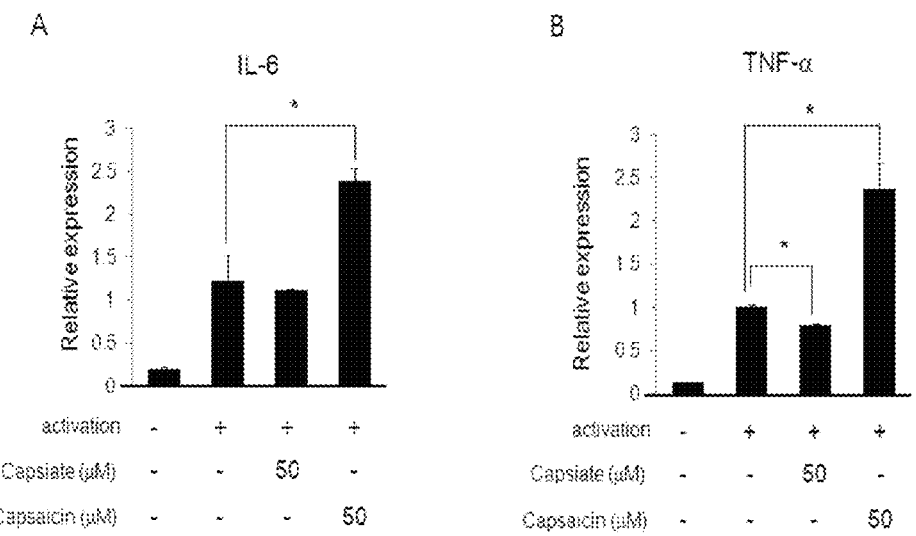
FIG. 1 shows real-time PCR results of the inhibitory effect of capsiate on the increase in cytokines in the activated human mast cell line (HMC-1 cells) (A: IL-6; and B: TNF-α)

Hereinafter, the present invention will be described in detail.

However, the following examples are merely for illustrating the present invention, and are not intended to limit the scope of the present invention.

In order to accomplish these objects, there is provided a method for preventing or treating allergic diseases, the method comprising administering to a subject in need thereof an effective amount of capsiate or a pharmaceutically acceptable salt thereof.

In accordance with another aspect of the present invention, there is provided a method for preventing, alleviating, or treating allergic skin diseases, the method comprising contacting with a subject in need thereof an effective amount of capsiate or a salt thereof.

Hereinafter, the present invention will be described in detail.

The present invention provides a method for preventing or treating allergic diseases, the method comprising administering to a subject in need thereof an effective amount of capsiate or a pharmaceutically acceptable salt thereof.

The capsiate according to the present invention has a structure represented by Chemical Formula 1. The capsiate may be separated and purified from its natural source, commercially purchased and used, or prepared by chemical synthetic methods known in the art.

<Chemical Formula 1>

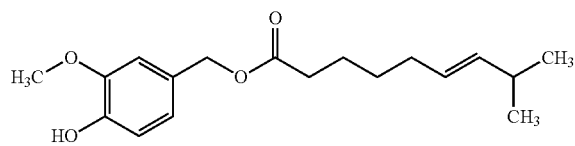

Preferably, capsiate may be separated and purified from its natural source. More preferably, capsiate may be separated and purified from CH19 Sweet, which is a variety of mildly spicy pepper. The capsiate according to the present invention may be extracted by known methods generally used in the art, such as extraction with organic solvent, chromatography, and the like.

In an example of the present invention, the inhibitory effect of capsiate on the increase in cytokines in the activated human mast cell line (HMC-1 cells) was researched. As a result, the increased expressions of cytokines IL-6 and TNF-α in the HMC-1 cells were increased by the treatment with capsaicin, but reduced by the treatment with capsiate.

In addition, the capsaicin has been known as a material inducing an allergic reaction, and an example of the present invention verified that capsaicin further increases the expressions of cytokines IL-6 and TNF-α in the HMC-1 cells. Thus, it could be concluded that the capsiate has an anti-allergic effect in the activated HMC-1 cells (See Example 1, and FIGS. 1 & 2).

In another example of the present invention, the inhibitory effect of capsiate on the increase in cytokines in the activated mouse bone marrow derived mast cells (BMMCs) was researched. As a result, the increased expressions of cytokines IL-6 and TNF-α in BMMCs were further increased by the treatment with capsaicin, but reduced by the treatment with capsiate.

The capsaicin has been known as a material inducing an allergic reaction as described above, and the present invention verified that capsaicin further increases the expressions of cytokines IL-6 and TNF-α in the BMMCs. Thus, it could be concluded that the capsiate has an anti-allergic effect in the activated BMMCs (See Example 2, and FIGS. 3 & 4).

Figure 5:
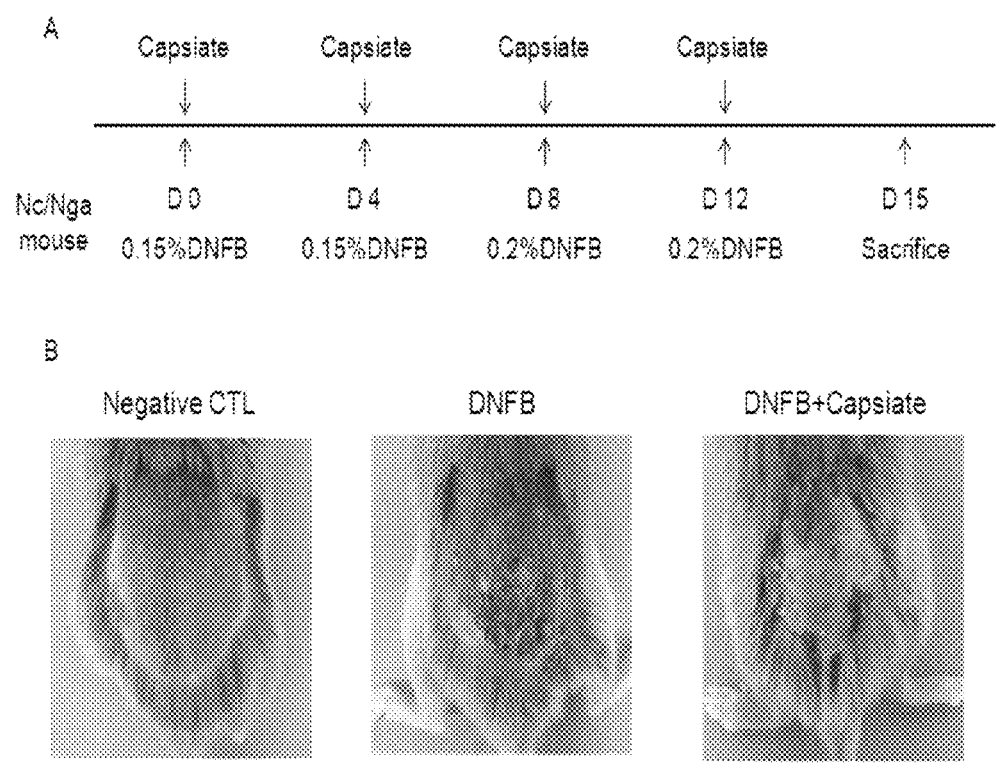
FIG. 5 shows the inhibitory effect of capsiate on the atopic dermatitis induced by 2,4-dinitro-1-fluorobenzene (DNFB) in mice (A: DNFB administration method; and B: mouse experimental results images)

In still another example of the present invention, the inhibitory effect of capsiate on the atopic dermatitis induced by 2,4-dinitro-1-fluorobenzene (DNFB) in mice was researched. DNFB is known as a material inducing atopic dermatitis in Nc/Nga mice, and thus was employed as an atopic dermatitis-causing material in the present application. As a result, it was confirmed that the atopic dermatitis induced by DNFB in the mice was inhibited by capsiate (See Example 3 and FIGS. 5 & 6). Another example of the present invention also verified the effect of capsiate on reducing the level of serum IgE in an atopic dermatitis mouse model induced by DNFB (See Example 4 and FIG. 7). The serum IgE is a serum immunoprotein, and the serum IgE level is increased mainly by allergic diseases and immune diseases. The serum IgE is known to be a material that stimulates mast cells to secrete histamine.

In still another example of the present invention, the cytokine and chemokine inhibitory effects of capsiate in the sites of the mouse atopic dermatitis were researched. As a result, it was found that the increased expressions of cytokines IL-4 & TSLP and chemokines CCL11, CCL17, and CCL22 in the sites of the mouse atopic dermatitis caused by DNFB were reduced by the treatment with capsiate (See Example 5 and FIGS. 8 & 9).

In still another example of the present invention, the Th2 cell differentiation inhibitory effect of capsiate in the atopic dermatitis mouse model was researched. The differentiation of Th2 cells occurs in an immune hypersensitivity reaction state, and it was found that the Th2 cell differentiation was inhibited by capsiate in the spleen and lymph nodes of the atopic dermatitis mouse model induced by DNFB (See Example 6 and FIGS. 10 & 11).

In still another example of the present invention, the passive cutaneous anaphylaxis (PCA) inhibitory effect of capsiate was researched. As a result, it was found that the edema of mouse ear induced by IgE was inhibited by capsiate (See Example 7 and FIG. 12).

In still another example of the present invention, the pro-inflammatory cytokine expression inhibitory effect of capsiate in activated BMMCs was researched. As a result, it was found that the increased expressions of cytokines IL1-β, IL-6, and TNF-α in BMMCs activated by IgE, were inhibited by capsiate (See Example 8 and FIG. 13).

Therefore, the present invention provides a method for preventing or treating allergic diseases, the method comprising administering an effective amount of capsiate or a pharmaceutically acceptable salt thereof to a subject in need thereof.

Capsiate according to the present invention may be used as it is or in the form of its pharmaceutically acceptable salt. The term "pharmaceutically acceptable" means that a substance is physiologically acceptable and usually does not invoke any allergic or similar reactions when administered to humans. Preferably, the salt may be an acid addition salt formed from a pharmaceutically acceptable free acid. The free acid may be an organic or inorganic acid. The organic acid includes, but is not limited to, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. In addition, the inorganic acid includes, but is not limited to, hydrochloric acid, bromic acid, sulfuric acid and phosphoric acid.

Examples of the allergic diseases, to which the compound according to the present invention can be applied, include, but are not limited to, atopic dermatitis, urticaria, mastocytosis, allergic skin diseases, bronchial asthma, allergic rhinitis, and allergic mucositis.

In addition, examples of the allergic skin diseases include, but are not limited to, atopic dermatitis, allergic dermatitis, allergic contact dermatitis, eczema, mastocytosis, urticaria, toxicodermatosis, drug rash, lupus erythematosis, and skin granulomatous disease.

In the method for prevention or treatment according to the present invention, capsiate or pharmaceutical acceptable salt thereof may be used alone or in combination with at least one pharmaceutically acceptable carrier, an excipient, or a diluent.

A pharmaceutically acceptable carrier, for example, carriers for parenteral or oral preparations may be comprised. The carriers for the oral preparations may comprise lactose, starch, cellulose derivatives, magnesium stearate, stearic acid and the like, while the carriers for the parenteral preparations may comprise water, suitable oil, saline, aqueous glucose and glycol and the like. The examples of the stabilizers may be anti-oxidizing agents such as sodium hydrogen sulfite, sodium sulfite, and ascorbic acid. The examples of the preservatives may be benzalkonium chloride, methyl- or prophyl-paraben, and chlorobutanol. The list of pharmaceutically acceptable carriers is disclosed in Remington's Pharmaceutical Sciences, 19th ed., Mack Publishing Company, Easton, Pa., 1995.

Capsiate or pharmaceutically acceptable salt thereof according to the present invention may be administered to mammalian animals including humans by any routes, for example, oral or parenteral routes. The parenteral routes include, but not limited thereto, intravenous, intramuscular, intraarterial, intramarrow, intra pachymeninx, intracardiac, transdermal, subcutaneous, peritorial, intranasal, gastrointestinal tracts, sublingual or rectal route. Preferably, the capsiate or pharmaceutically acceptable salt thereof of the present invention may be injected through transdermal administration. As used herein, the term "transdermal administration" refers to administering the capsiate or pharmaceutically acceptable salt of the present invention to cells or the skin of a subject to deliver the active ingredient of the present invention into the skin. For example, the capsiate or pharmaceutically acceptable salt of the present invention is prepared into an injectable formulation, which may then be administered by slightly pricking the skin using a 30-gauge thin injection needle, or by being applied directly onto the skin.

Capsiate or pharmaceutically acceptable salt thereof of the present invention may be formulated into preparations for oral or parenteral administration as described above.

In case of the formulation for oral administration, capsiate or pharmaceutically acceptable salt thereof of the present invention may be formulated into powders, granules, tablets, pills, and sugar-coated tablets, capsules, liquids, gels, syrups, slurries, emulsions and the like by using the methods known in the art. For instance, oral preparations may be obtained as a form of tablet or sugar-coated tablet by mixing the active ingredient with solid carriers, being ground and added with suitable adjuvants, followed by being processed into a granule mixture. Examples of appropriate carriers may include sugars including lactose, dextrose, sucrose, sorbitol, mannitol, xylitol, erythritol and maltitol; starches including corn starch, wheat starch, rice starch and potato starch; celluloses including cellulose, methyl cellulose, sodium carboxymethylcellulose and hydroxypropylmethylcellulose; and fillers including gelatin and polyvinylpyrrolidone. And, if desired, it may include cross-linked polyvinylpyrrolidone, agar, alginic acid or sodium alginate as a solutionizer. Further, capsiate or pharmaceutically acceptable salt thereof of the present invention may be formulated with anti-coaglutinating agents, lubricants, wetting agents, flavors, emulsifying agents, antiseptics and the like.

In case of parenteral preparation, capsiate or pharmaceutically acceptable salt thereof of the present invention may be formulated into injections, creams, lotions, ointments, oils, humectants, gels, aerosols and nasal inhaler by the known methods in the art. These formulations are described in the Remington's Pharmaceutical Science, 15th Edition, 1975, Mack Publishing Company, Easton, Pa., which is well known in the pharmaceutical chemistry field.

Total effective amount of capsiate or pharmaceutically acceptable salt thereof of the present invention may be administered to a patient in a single dose, or in multiple doses by fractionated treatment protocol. Capsiate or pharmaceutically acceptable salt thereof of the present invention may be employed in its variable amount as the effective ingredient according to the severity of disease. In case of oral preparation, the total amount of capsiate according to the present invention is preferably about 0.000001 µg to 1,000 mg/kg body weight/day, more preferably about 0.1 µg to 100 mg/kg body weight/day. In case of parenteral preparation, the total amount of capsiate or pharmaceutically acceptable salt thereof of the present invention is preferably 0.000001 to 1000 mM capsiate/day which may be applied to the sites of disease. However, the effective dose of capsiate or pharmaceutically acceptable salt thereof according to the present invention may be suitably determined by considering various factors, such as age, body weight, health condition, sex, disease severity, diet and excretion of a subject in need of treatment, as well as administration frequency and administration route. When those factors are considered, the skilled person in the art may determine appropriate effective dose of capsiate or pharmaceutically acceptable salt thereof according to the present invention for the purpose of preventing or treating allergic diseases. Capsiate or pharmaceutically acceptable salt thereof according to the present invention may not be limited by the type of formulation, the route of administration, and the method of administration as long as it maintains its effectiveness in accordance with the present invention.

As used herein, the term "effective amount" refers to an amount which exhibits the effect of preventing, alleviating or treating allergic diseases upon being administered to a subject. The term "a subject" refers to an animal, preferably a mammalin animal including humans, while including cells, tissues or organs originated from an animal. The "subject" may be a patient in need of treatment. In addition, as used herein, the term "a subject in need thereof" refers to a subject in need of the prevention or treatment of allergic diseases.

Furthermore, the present invention provides a method for preventing, alleviating, or treating allergic skin diseases, the method comprising contacting with a subject in need thereof an effective amount of capsiate or a salt thereof.

As used herein, the term "effective amount" refers to an amount which exhibits the effect of preventing, alleviating or treating allergic skin diseases upon being in contact with a subject. The term "a subject" refers to an animal, preferably a mammalin animal including humans, while including cells, tissues or organs originated from an animal. The "subject" may be a patient in need of prevention, alleviation or treatment. In addition, as used herein, the term "a subject in need thereof" refers to a subject in need of the prevention, alleviation or treatment of allergic skin diseases. As used herein, the term "contact" is a term including a direct contact with the skin of a subject, including the application on the skin of the subject in need thereof. In addition, as to the salt of capsiate, any form of its dermatologically acceptable salt may be used without limitation, while its pharmaceutically acceptable salt is preferable.

Capsiate or its salt according to the present invention may be prepared in the form of basic cosmetics (lotions, cream, essence, cleansers such as cleansing foam and cleansing water, pack, body oil), coloring cosmetics (foundation, lipstick, mascara, make-up base), hair care composition (shampoo, rinse, hair conditioner, hair gel) and soap with dermatologically acceptable excipients.

The said excipients may include, but not limited thereto, skin softener, skin infiltration enhancer, colorant, odorant, emulsifier, thickener, or solvent. In addition, it may further include a fragrance, a pigment, bactericidal agent, an antioxidant, a preservative, moisturizer and the like, while including thickening agents, inorganic salts, synthetic polymers and the like for improving physical properties. For example, in case of manufacturing a cleanser and soap comprising capsiate or its salt according to the present invention, they may be prepared easily by adding capsiate or its salt to conventional cleanser or soap base. In case of manufacturing a cream, it may be prepared by adding capsiate or its salt to conventional oil-in-water cream base. In addition, it may further include a fragrance, a chelating agent, a pigment, an antioxidant, a preservative, and the like, as well as synthetic or natural proteins, minerals or vitamins for improving physical properties.

Capsiate or it salt may be prepared in the form of cosmetic composition, while the amount of capsiate or its salt in a cosmetic formulation is preferably in the range of 0.0001-50 wt %, and more preferably 0.01-5 wt %, based on the total weight of a formulation. Using an amount of less than 0.001 wt % may not achieve a desired effect of preventing or alleviating an allergic skin condition, whereas using an amount of more than 50 wt % may not result in an effect proportionate to the amount used.

In addition, examples of the allergic skin diseases include, but are not limited to, atopic dermatitis, allergic dermatitis, allergic contact dermatitis, eczema, mastocytosis, urticaria, toxicodermatosis, drug rash, lupus erythematosis, skin granulomatous disease, and the like.

EXAMPLE 1

Inhibitory Effect of Capsiate on Increase of Cytokines in Activated Human Mast Cell Line (HMC-1 Cells)

<1-1> Cell Culture and Activation

HMC-1 cells were grown in IMDM media supplemented with 100 U/ml of penicillin, 100 lg/ml of streptomycin, and 10% heat-inactivated FBS in an incubator containing 5% $CO_2$ at 37° C. HMC-1 cells were activated by treatment with A23187 and PMA <1-2> Real-Time PCR Assay In order to understand the inhibitory effect of capsiate on the increase of cytokines in activated HMC-1 cells, HMC-1 cells were treated with 50 µM of capsiate and capsaicin at 37° C. for 4 hours, respectively, and the transcript expressions of cytokines IL-6 and TNF-α were confirmed through real-time PCR. Total RNA was isolated from HMC-1 cells with RNeasy Mini kit (Quiagen, Valencia, Calif., USA) and the first strand of cDNA was synthesized using QuantTect Reverse Transcription kit (Quiagen, Germany). Real-time PCR was performed using KAPA SYBR fast qPCR kit (KAPA Blosystems, Woburn, Mass., USA). The following parameters were used for the PCR: 95° C. for 10 minutes, followed by 50 cycles of 95° C. for 20 seconds, 55° C. for 30 seconds, and 72° C. for 20 seconds. The gene expression levels were normalized with GAPDH expression level. The primer sets for IL-6 and TNF-α were purchased from QIAGEN.

As a result, as shown in FIG. 1, the expressions of IL-6 and TNF-α increased for capsaicin-treated group, but significantly decreased for capsiate-treated group.

<1-3> ELISA Assay

In order to understand the inhibitory effect of capsiate on the increase of cytokines in activated HMC-1 cells, HMC-1 cells were treated with 50 µM of capsiate and capsaicin at 37° C. for 16 hours, and the expression levels of cytokines IL-6 and TNF-α were confirmed through ELISA assay. Capture antibody was added in ELISA plate and incubated overnight 4° C. Next day, the capture antibody was washed with PBS/Tween buffer, and blocking buffer was added. After 1 hr incubation at room temperature, the blocking buffer was washed out and standard or sample supernatant was added. The plate was incubated overnight at 4° C. and washed out. After washing, detection antibody was added and incubated for 1 hr at room temperature, followed by washing the plate. Streptavidin-HRP was added to each well, incubated at room temperature for 30 mins, and then the plate was washed. TMB was used as a substrate. After TMB was added to the plate, stop solution was added to stop color development, and the plate was read using ELISA reader.

Figure 2:
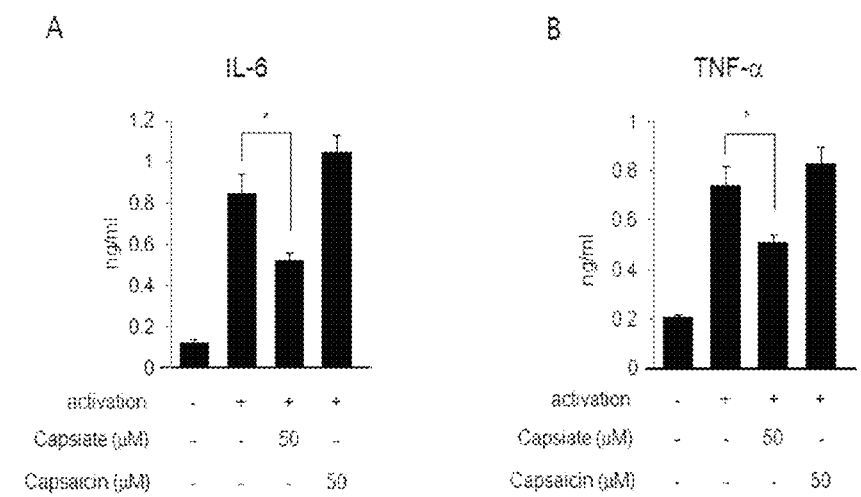
FIG. 2 shows ELISA results of the inhibitory effect of capsiate on the increase in cytokines in the activated HMC-1 cells (A: IL-6; and B: TNF-α)

As a result, as shown in FIG. 2, the expressions of IL-6 and TNF-α increased for capsaicin-treated group, but significantly decreased for capsiate-treated group.

EXAMPLE 2

Inhibitory Effect of Capsiate on the Increase of Cytokines in Activated Mouse Bone Marrow Derived Mast Cells (BMMCs)

<2-1> Cell Culture and Activation

Bone marrow cells were obtained from tibias and femurs of approximately 8 to 10 week old C57/BL/6 mice and cultured in RPMI 1640 media supplemented with 10% FCS, 100 U/ml of penicillin, 100 µg/ml of streptomycin in the presence of mIL-3 (10 ng/ml) and mSCF (50 ng/ml) for 6 weeks in an incubator containing 5% $CO_2$ at 37° C. FACS analysis showed that >97% of the cells were mast cells (CD117 (c-kit) and FceRI positive). BMMC were activated by 1 µg/ml of anti-mouse DNP-IgE for overnight, followed by the treatment with 10 ng/ml of DNP-HSA for 6 hr to 24 hr.

<2-2> Real time PCR

In order to understand the inhibitory effect of capsiate on the increase in cytokines in activated BMMCs, BMMCs were treated with 50 µM of capsiate at 37° C. for 4 hours, and the transcript expressions of cytokines IL-6 and TNF-α were confirmed through real-time PCR. Total RNAs were isolated from HMC-1 cells with RNeasy Mini kit (Quiagen, Valencia, Calif., USA) and the first strand of cDNA was synthesized using QuantTect Reverse Transcription kit (Quiagen, Germany). Real-time PCR was performed using KAPA SYBR fast qPCR kit (KAPA Blosystems, Woburn, Mass., USA). The following parameters were used for the PCR: 95° C. for 10 mins, followed by 50 cycles of 95° C. for 20 s, 55° C. for 30 s, and 72° C. for 20s. The gene expression levels were normalized with GAPDH expression level. The primer sets for IL-6 and TNF-α were purchased from QIAGEN.

Figure 3:
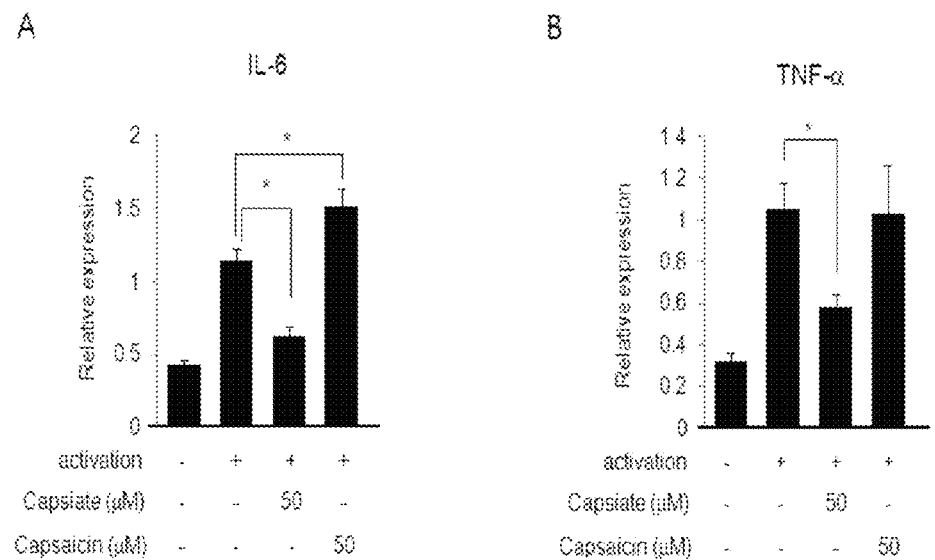
FIG. 3 shows real-time PCR results of the inhibitory effect of capsiate on the increase in cytokines in the activated mouse bone marrow derived mast cells (BMMCs) (A: IL-6; and B: TNF-α)

As a result, as shown in FIG. 3, the expressions of IL-6 and TNF-α increased for capsaicin-treated group, but significantly decreased for capsiate-treated group.

<2-3> ELISA Assay

In order to understand the inhibitory effect of capsiate on the increase of cytokines in activated BMMCs, BMMCs were treated with 50 μM of capsiate at 37° C. for 16 hours, and the expression levels of cytokines IL-6 and TNF-α were confirmed through ELISA assay. Capture antibody for IL-6 or TNF-α was added in ELISA plate and incubated overnight 4° C. Next day, the capture antibody was washed with PBS/Tween buffer, and blocking buffer was added. After 1 hr incubation at room temperature, the blocking buffer was washed out and standard or sample supernatant was added. The plate was incubated overnight at 4° C. and washed out. After washing, detection antibody for IL-6 and TNF-α was added and incubated for 1 hr at room temperature, followed by washing the plate. Streptavidin-HRP was added to each well, incubated at room temperature for 30 mins, and then the plate was washed. TMB was used as a substrate. After TMB was added to the plate, stop solution was added to stop color development, and the plate was read using ELISA reader.

Figure 4:
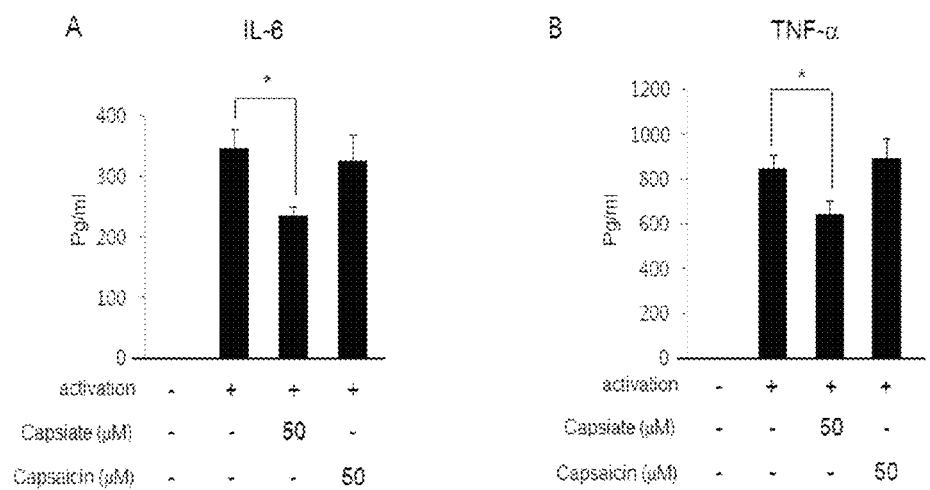
FIG. 4 shows ELISA results of the inhibitory effect of capsiate on the increase in cytokines in the activated mouse bone marrow derived mast cells (BMMCs) (A: IL-6; and B: TNF-α)

As a result, as shown in FIG. 4, the expressions of IL-6 and TNF-α increased for capsaicin-treated group, but significantly decreased for capsiate-treated group.

EXAMPLE 3

Inhibitory Effect of Capsiate on Atopic Dermatitis Induced by 2,4-Dinitro-1-Fluorobenzene (DNFB) in Mice <3-1> Treatment Method of DNFB and Capsiate DNFB was sensitized by being diluted to 0.15% with a vehicle in which acetone and olive oil are mixed in a ratio of 3:1. Atopic dermatitis was induced by treating twice with a 0.2% DNFB solution. The capsiate-treated group was coated with 1 mM capsiate dissolved in acetone, 1 hour before DNFB treatment (See FIG. 5).

<3-2> Histological Staining and Epidermal Thickness Measurement

After being cut with induced atopic dermatitis, the skin tissue was fixed in 4% formaldehyde for 24 hours, followed by washing and dehydration, and then a 0.5 μm-thick skin section was prepared using a paraffin block. The tissue section was deparaffinized with xylene, immerged in alcohol, and then stained with hematoxyline and eosin. After the staining, the tissue was observed using a phase contrast microscope. As for the dermal thickness, the dermal thicknesses at five places on the tissue image were measured, and the mean and standard deviation thereof were obtained and shown on a graph.

Figure 6:
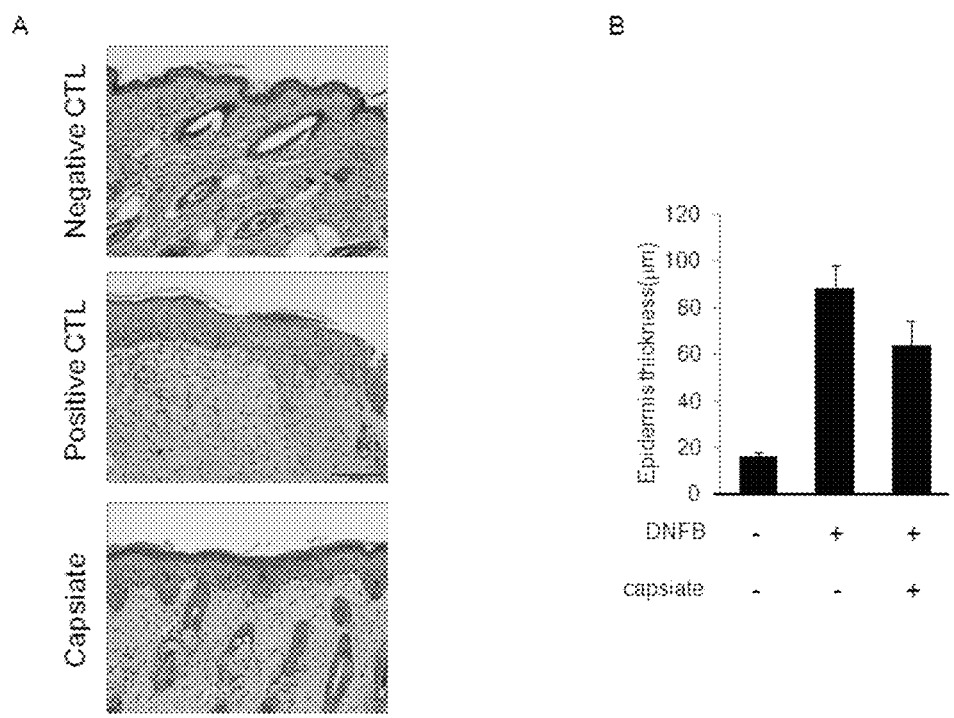
FIG. 6 shows the inhibitory effect of capsiate on the atopic dermatitis induced by 2,4-dinitro-1-fluorobenzene (DNFB) in mice (A: histological staining results; and B: epidermal thickness)

As a result, as shown in FIG. 6, it was verified that the dermal thickness increased by DNFB decreased by capsiate.

EXAMPLE 4

Effect of Capsiate on Reducing the Level of Serum IgE in Atopic Dermatitis Mouse Model Induced by DNFB IgE capture antibody was added in the plate, and allowed to stand at 4° C. overnight. The next day, the capture antibody was washed with PBS/Tween buffer, and blocking buffer was added, followed by reaction at room temperature for 1 hour. After the blocking buffer was washed out, IgE standard and mouse serum were added, followed by standing at 4° C. overnight. The next day, after washing was performed, the IgE detection antibody was added, followed by reaction at room temperature for 1 hour. After washing was again performed, Streptavidin-HRP was added, followed by a reaction at room temperature for 30 minutes. After washing was again performed, TMB as a substrate was added. Then, a stop solution was added, and the absorbance was measured using an ELISA reader.

Figure 7:
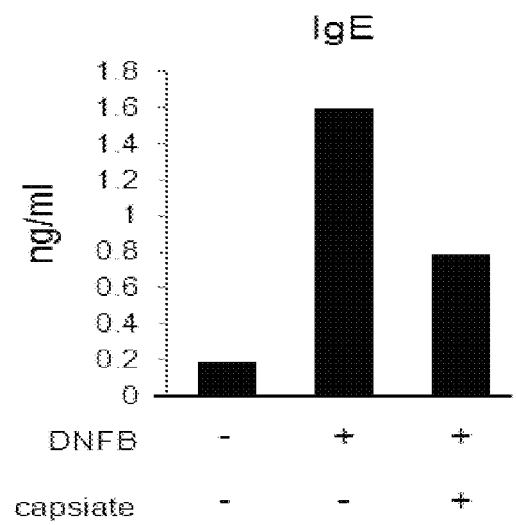
FIG. 7 shows the effect of capsiate on reducing the level of serum IgE in the atopic dermatitis mouse model induced by DNFB.

As a result, as shown in FIG. 7, it was found that the increased level of IgE due to DNFB decreased by treating with capsiate.

EXAMPLE 5

Cytokine and Chemokine Inhibitory Effects of Capsiate in Mouse Atopic Dermatitis Sites <5-1> Cytokine Inhibitory Effect The cytokine inhibitory effect of capsiate was verified at atopic dermatitis sites of mice. The dosing concentrations of DNFB and capsiate were the same as in example <3-1> above, and the transcript expressions of cytokines IL-4 and TSLP were confirmed through real-time PCR. Real-time PCR conditions were established by the same method as in example <1-2> above, and the primer set was purchased from QIAGEN.

Figure 8:
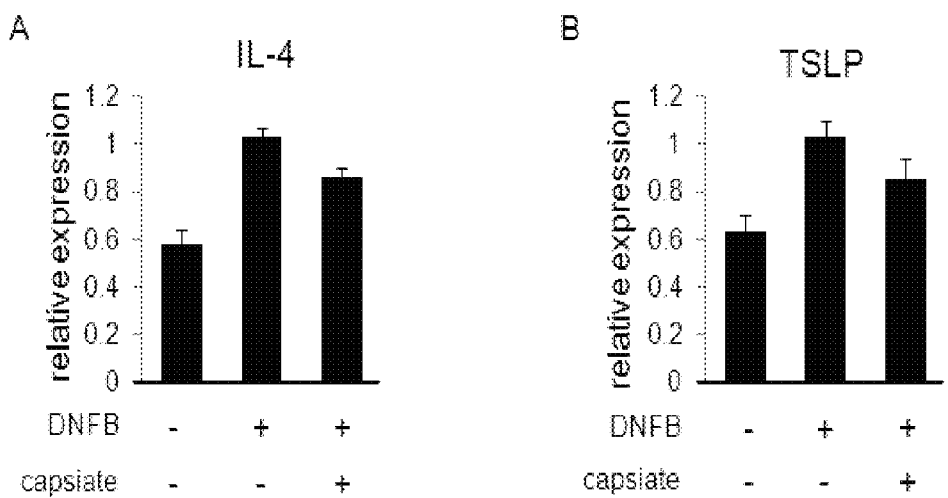
FIG. 8 shows real-time PCR results of the cytokine expression inhibitory effect of capsiate in the mouse atopic dermatitis site (A: IL-4; and B: TSLP)

As a result, as shown in FIG. 8, it was found that the cytokine expression increased by DNFB decreased by treating with capsiate.

<5-2> Chemokine inhibitory effect

The chemokine inhibitory effect of capsiate in atopic dermatitis sites of mice was verified. The dosing concentrations of DNFB and capsiate were the same as in example <3-1> above, and the transcript expressions of chemokines CCL11, CCL17, and CCL22 were confirmed through real-time PCR. Real-time PCR conditions were established by the same method as in example <1-2> above, and the primer set was purchased from QIAGEN.

Figure 9:
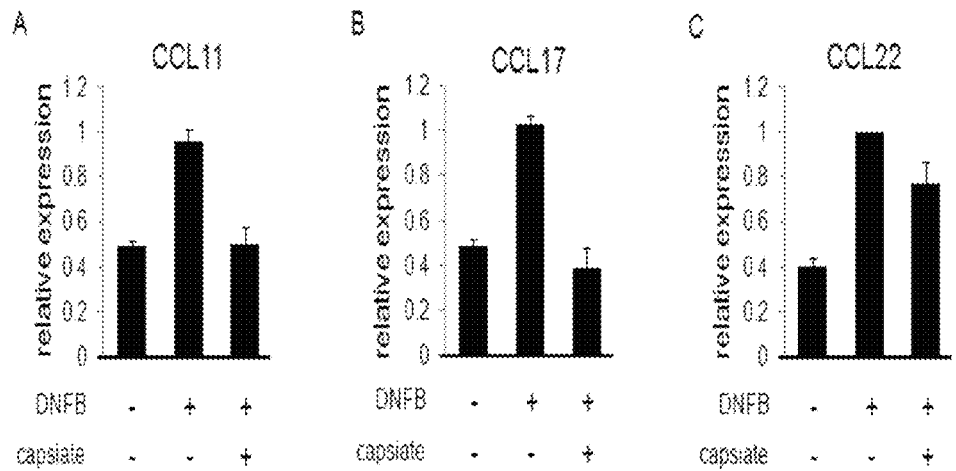
FIG. 9 shows real-time PCR results of the chemokine expression inhibitory effect of capsiate in the mouse atopic dermatitis site (A: CCL11; B: CCL17; and C: CCL22)

As a result, as shown in FIG. 9, it was found that the chemokine expression increased by DNFB decreased by treating capsiate.

EXAMPLE 6

Th2 Cell Differentiation Inhibitory Effect of Capsiate in Atopic Dermatitis Mouse Model <6-1> Lymph Node After lymphocytes were taken out from mice, a single cell suspension was prepared, and then 3 μg/ml of anti-CD28 antibody was added in the plate to which anti-CD3 antibody adheres, followed by incubation for 3 days. On the third day, PMA (20 ng/ml) and ionomycin (1 μM) were added, followed by incubation for 5 hours. The cells were collected, and then subjected to intracellular staining using Cytofix/Cytoperm kit (BD bioscience) and anti-CD4 antibody, anti-IL-4 antibody, and anti-IL-5 antibody (BD bioscience). The dosing concentrations of DNFB and capsiate were the same as in example <3-1> above.

Figure 10:
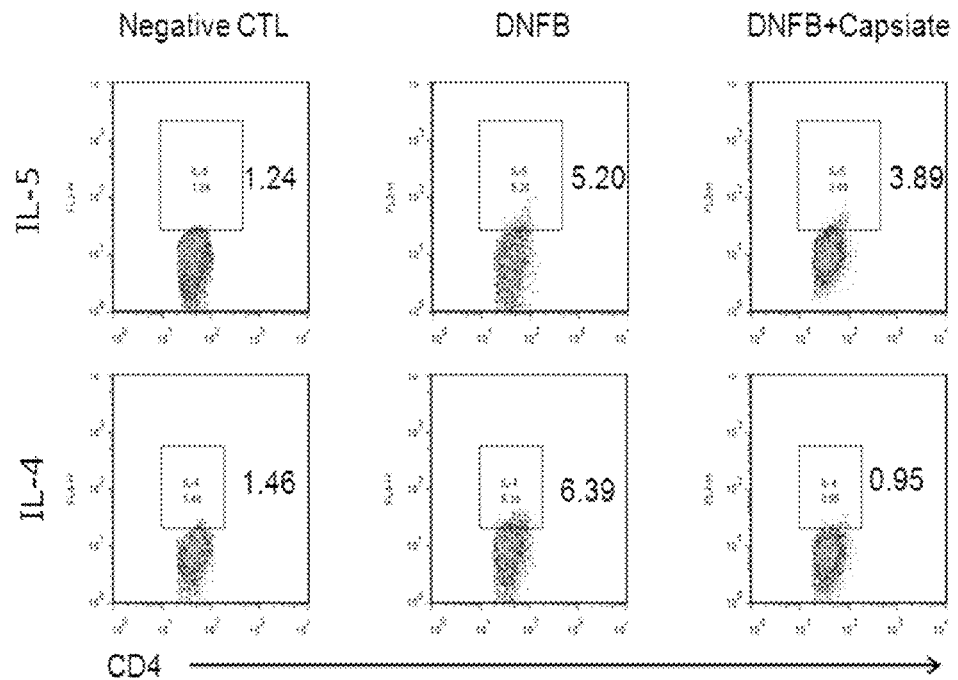
FIG. 10 shows the Th2 cell differentiation inhibitory effect of capsiate in the lymph node of the atopic dermatitis mouse model.

As a result, as shown in FIG. 10, it was verified that the Th2 cell differentiation increased by DNFB at the lymph node was inhibited by capsiate.

<6-2> Spleen

After the spleen was taken out from mice, a single cell suspension was prepared, and then 3 μg/ml of anti-CD28 antibody was added in the plate to which anti-CD3 antibody adheres, followed by incubation for 3 days. On the third day, PMA (20 ng/ml) and ionomycin (1 μM) were added, followed by incubation for 5 hours. The cells were collected, and then subjected to intracellular staining using Cytofix/Cytoperm kit (BD bioscience) and anti-CD4 antibody, anti-IL-4 antibody, and anti-IL-5 antibody (BD bioscience). The dosing concentrations of DNFB and capsiate were the same as in example <3-1> above.

Figure 11:
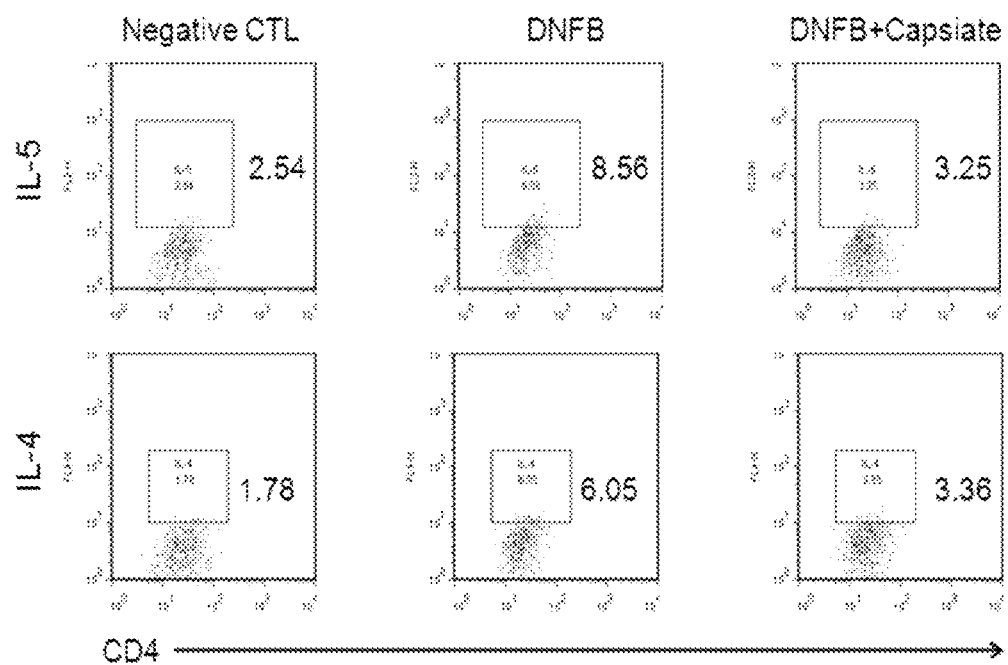
FIG. 11 shows the Th2 cell differentiation inhibitory effect of capsiate in the spleen of the atopic dermatitis mouse model.

As a result, as shown in FIG. 11, it was verified that the Th2 cell differentiation increased by DNFB in the spleen was inhibited by capsiate.

EXAMPLE 7

Passive Cutaneous Anaphylaxis (PCA) Inhibitory Effect of Capsiate

The passive cutaneous anaphylaxis inhibitory effect of capsiate was verified by measuring capillary vessel permeability and mouse ear thickness. The capillary vessel permeability was verified by intravenously injecting Evan's blue, which is a blue staining agent, mixed with antigen, and quantifying the staining agent coming out from ear capillary vessels to the skin tissue. The quantification was conducted by cutting the ear tissue, putting the cut ear tissue in formamide, performing incubation at 65° C. for 16 hours, extracting Evan's blue in the ear tissue, and measuring the absorbance. The mouse ear thickness was measured using D15 ear thickness gauge.

Figure 12:
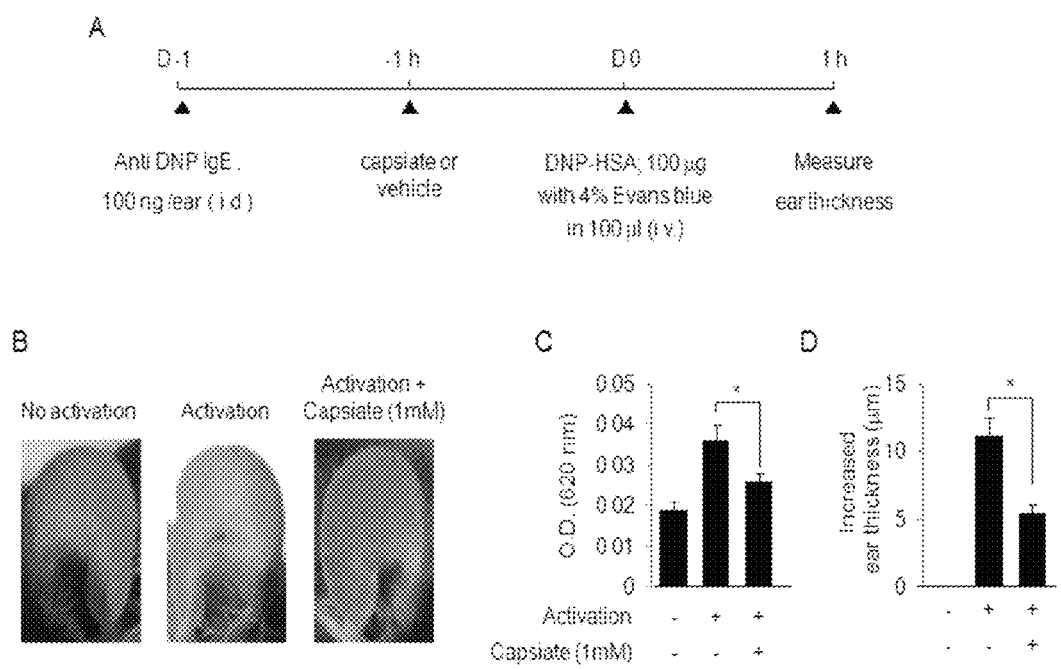
FIG. 12 shows results of the passive cutaneous anaphylaxis (PCA) inhibitory effect of capsiate through measurement of capillary vessel permeability and mouse ear thickness (A: experimental method; B: mouse ear images; C: capillary vessel permeability; and D: ear thickness)

As a result, as shown in FIG. 12, it was verified that capillary vessel permeability and ear edema, increased by DNP lgE, were inhibited by capsiate.

EXAMPLE 8

Pro-inflammatory Cytokine Expression Inhibitory Effect of Capsiate in Activated BMCC The inflammatory cytokine expression inhibitory effect of capsiate was verified in BMCC induced with IgE antigen. The transcript expressions of cytokines IL-1β, IL-6, and TNF-α were verified through real-time PCR. Real-time PCR conditions were established by the same method as in example <1-2> above, and the primer set was purchased from QIAGEN.

Figure 13:
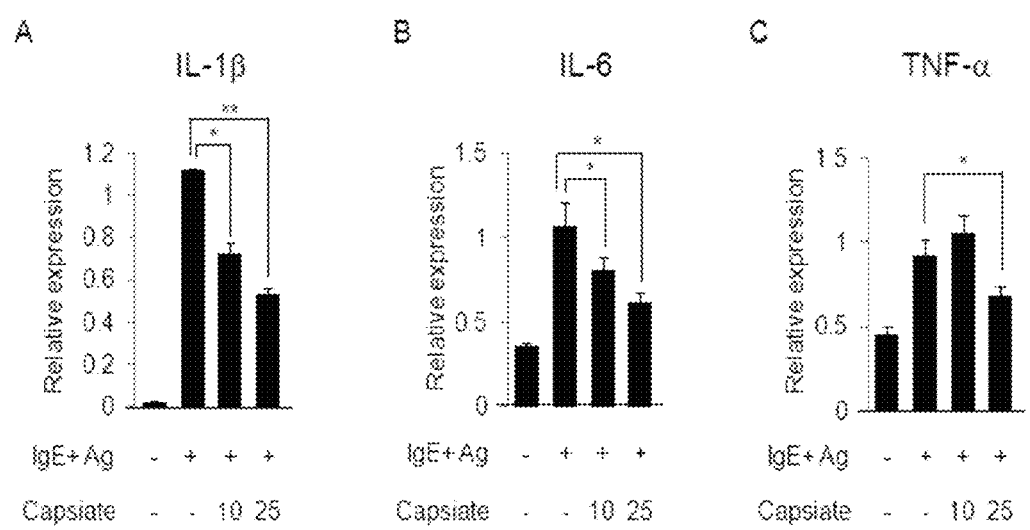
FIG. 13 shows the pro-inflammatory cytokine expression inhibitory effect of capsiate in activated BMCCs (A: IL-1β; B: IL-6; and C: TNF-α).

As a result, as shown in FIG. 13, it could be verified that the chemokine expression increased by IgE antigen decreased by capsiate.

The invention claimed is:

1. A method for alleviating or treating an allergic disease, the method comprising administering to a subject in need thereof an effective amount of capsiate represented by Chemical Formula 1 or a pharmaceutically acceptable salt thereof

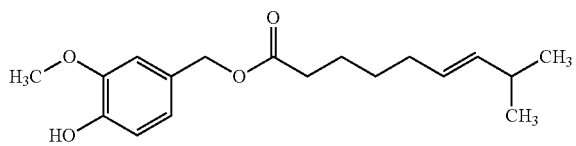

<Chemical Formula 1> wherein the allergic disease is induced by an activation of mast cells and selected from the group consisting of mastocytosis and allergic mucositis.

2. A method for alleviating or treating an allergic skin disease, the method comprising contacting with a subject in need thereof an effective amount of capsiate represented by Chemical Formula 1 or a salt thereof

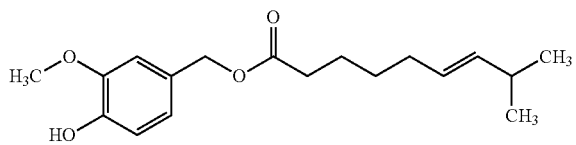

<Chemical Formula 1> wherein the allergic skin disease is induced by an activation of mast cells and selected from the group consisting of mastocytosis, toxicodermatosis, drug rash, and lupus erythematosis.

* * * * *